(12) United States Patent
Kang et al.

(10) Patent No.: US 12,338,422 B2
(45) Date of Patent: Jun. 24, 2025

(54) THREE-DIMENSIONAL BIOMIMETIC CHIP FOR SIMULATING ENDOMETRIUM, AND ENDOMETRIUM SIMULATING METHOD USING SAME

(71) Applicants: CHA UNIVERSITY INDUSTRY-ACADEMIC COOPERATION FOUNDATION, Pocheon-si (KR); SUNGKWANG MEDICAL FOUNDATION, Seoul (KR)

(72) Inventors: Youn Jung Kang, Yongin-si (KR); Jung Ho Ahn, Seongnam-si (KR); Min Ji Yoon, Seoul (KR); Hwi Jae Cha, Seoul (KR); Seon Hwa Hong, Gyeonggi-do (KR)

(73) Assignees: CHA UNIVERSITY INDUSTRY-ACADEMIC COOPERATION FOUNDATION, Pocheon-si (KR); SUNGKWANG MEDICAL FOUNDATION, Seoul (KR)

(*) Notice: Subject to any disclaimer, the term of this patent is extended or adjusted under 35 U.S.C. 154(b) by 82 days.

(21) Appl. No.: 18/003,067

(22) PCT Filed: Jun. 23, 2021

(86) PCT No.: PCT/KR2021/007860
§ 371 (c)(1),
(2) Date: Dec. 22, 2022

(87) PCT Pub. No.: WO2021/261902
PCT Pub. Date: Dec. 30, 2021

(65) Prior Publication Data
US 2023/0332079 A1 Oct. 19, 2023

(30) Foreign Application Priority Data
Jun. 23, 2020 (KR) .................. 10-2020-0076780

(51) Int. Cl.
*C12M 3/00* (2006.01)
*C12M 3/06* (2006.01)

(52) U.S. Cl.
CPC ............ *C12M 21/08* (2013.01); *C12M 23/16* (2013.01)

(58) Field of Classification Search
None
See application file for complete search history.

(56) References Cited

U.S. PATENT DOCUMENTS

2011/0244567 A1   10/2011   Jeon et al.
2014/0093905 A1   4/2014    Ingber et al.
(Continued)

FOREIGN PATENT DOCUMENTS

CN   109381743 A   2/2019
CN   110551681 A   12/2019
(Continued)

OTHER PUBLICATIONS

Smith SK. Regulation of angiogenesis in the endometrium. Trends Endocrinol Metab. May-Jun. 2001;12(4):147-51. doi: 10.1016/s1043-2760(01)00379-4. PMID: 11295569. (Year: 2001).*
(Continued)

*Primary Examiner* — Allison M Fox
*Assistant Examiner* — Alyssa G Weston
(74) *Attorney, Agent, or Firm* — Oblon, McClelland, Maier & Neustadt, L.L.P.

(57) ABSTRACT

The present disclosure relates to a biomimetic chip for three-dimensionally simulating an endometrium, and an endometrium simulating method using the biomimetic chip.

(Continued)

The biomimetic chip according to an embodiment of the present disclosure is a three-dimensional biomimetic chip including a plate, a plurality of chambers, and a plurality of posts, which are arranged between the plurality of chambers, wherein the plurality of chambers include channels in which different cells are cultured, are arranged on the plate to be parallel to each other in one direction, and are arranged adjacent to each other such that at least some sections communicate with each other.

5 Claims, 16 Drawing Sheets

(56) References Cited

U.S. PATENT DOCUMENTS

| | | |
|---|---|---|
| 2016/0257918 A1 | 9/2016 | Chapman et al. |
| 2017/0355945 A1 | 12/2017 | Kamm et al. |
| 2018/0312810 A1 | 11/2018 | Huh et al. |
| 2019/0133109 A1 | 5/2019 | Lee et al. |
| 2021/0032584 A1 | 2/2021 | Chung et al. |

FOREIGN PATENT DOCUMENTS

| | | | | |
|---|---|---|---|---|
| EP | 2526978 A1 | * | 11/2012 | ............. A61F 2/062 |
| KR | 10-1401199 B1 | | 5/2014 | |
| KR | 10-2015-0139022 A | | 12/2015 | |
| KR | 10-1965076 B1 | | 4/2019 | |
| KR | 10-2019-0050360 A | | 5/2019 | |
| KR | 10-2021-0014464 A | | 2/2021 | |

OTHER PUBLICATIONS

Kim S, Chung M, Ahn J, Lee S, Jeon NL. Interstitial flow regulates the angiogenic response and phenotype of endothelial cells in a 3D culture model. Lab Chip. Oct. 18, 2016;16(21):4189-4199. doi: 10.1039/c6lc00910g. PMID: 27722679. (Year: 2016).*

Ahn J, Yoon MJ, Hong SH, Cha H, Lee D, Koo HS, Ko JE, Lee J, Oh S, Jeon NL, Kang YJ. Three-dimensional microengineered vascularised endometrium-on-a-chip. Hum Reprod. Sep. 18, 2021;36(10):2720-2731. doi: 10.1093/humrep/deab186. PMID: 34363466; PMCID: PMC8450871. (Year: 2021).*

Japanese Office Action issued Nov. 21, 2023 in Japanese Patent Application No. 2022-579672 (with English translation), 10 pages.

Jungho Ahn, et al., "Investigation on vascular cytotoxicity and extravascular transport of cationic polymer nanoparticles using perfusable 3D microvessel model", Acta Biomaterialia, vol. 76, 2018, pp. 154-163.

International Search Report issued Sep. 28, 2021 in PCT/KR2021/007860, filed on Jun. 23, 2021, 4 pages.

Korean Office Action issued Nov. 8, 2021 in KR 10-2020-0076780 (with English Translation), 8 pages.

Korean Written Decision on Registration issued Mar. 8, 2022 in KR 10-2020-0076780 (with English Translation), 8 pages.

Gnecco, J. S. et al. "Compartmentalized culture of perivascular stroma and endothelial cells in a microfluidic model of the human endometrium", Annals of biomedical engineering. 2017, vol. 45, pp. 1758-1769.

Wei-Xuan, L. et al. "Artificial Uterus on a Microfluidic Chip", Chinese Journal of Analytical Chemistry vol. 41, Issue 4, Apr. 2013, 6 pages.

Gnecco, J. S. et al. "Hemodynamic forces enhance decidualization via endothelial-derived prostaglandin E2 and prostacyclin in a microfluidic model of the human endometrium", Human Reproduction, vol. 34, No. 4, 2019, pp. 702-714.

Zhao, Y. et al. "Multi-Organs-on-Chips: Towards Long-Term Biomedical Investigations", Molecules, 2019, 22 pages.

Extended European Search Report dated Jul. 18, 2024, in European Patent Application No. 21828049.3 (8 pages).

* cited by examiner a b c a b c

THREE-DIMENSIONAL BIOMIMETIC CHIP FOR SIMULATING ENDOMETRIUM, AND ENDOMETRIUM SIMULATING METHOD USING SAME

TECHNICAL FIELD

Embodiments of the present disclosure relate to a biomimetic chip, and more particularly, to a biomimetic chip capable of three-dimensionally simulating an endometrium, and a method of simulating an endometrium by using the biomimetic chip.

BACKGROUND ART

An organ-on-a-chip is a type of microchip made by simulating a living organ, such as a heart, lungs, or a liver, and may implement a system for replicating cells constituting a real organ and an environment surrounding the organ so as to allow the organ to function. By using an organ-on-a-chip, the stability of a drug and the phenomena occurring during a process of delivering the drug may be efficiently identified by injecting the drug into a simulated living organ, and thus, compared to existing preclinical screening of a new drug, the physiological environment in which actual organs function may be effectively reflected. In addition, organs-on-chips have recently attracted attention because they can solve ethical issues arising from animal experiments, excessive time and costs, and inaccurate results.

Meanwhile, uterus-related diseases have recently become a serious issue, as the number of patients suffering endometriosis, which is one of the representative intractable uterine diseases, has increased by more than 35% from 80,000 in 2013 to 120,000 in 2017, and the number of infertility patients has also increased 2.5 times in 10 years. Accordingly, there is a need for a preclinical uterine platform capable of studying the causes of uterine-related diseases. However, because related-art organs-on-chips two-dimensionally implement cell culture or consider only particular cells, they are insufficient to simulate the biological composition and function of a real uterus.

The related art described above is technical information that the inventor(s) of the present disclosure has achieved to derive the present disclosure or has achieved during the derivation of the present disclosure, and thus, it cannot be considered that the related art has been published to the public before the filing of the present disclosure.

DISCLOSURE

Technical Problem

The present disclosure may provide a biomimetic chip with high biosimilarity to a real uterus by physically and chemically implementing the shape of real uterine tissue.

In addition, the present disclosure may provide a biomimetic chip capable of implementing physiological functions of uterine tissue by culturing a plurality of types of cells into the biomimetic chip without being limited to particular cells.

In addition, the present disclosure may provide a biomimetic chip capable of simulating the organic properties of a real uterus by implementing an environment in which cells self-assemble into tissue through multi-layered culture channels so as to increase the physiological similarity with the real intrauterine environment.

However, this is an example, and the objects of the present disclosure are not limited thereto.

Technical Solution

A biomimetic chip according to an embodiment of the present disclosure is a three-dimensional biomimetic chip including a plate, a plurality of chambers, and a plurality of posts, which are arranged between the plurality of chambers, wherein the plurality of chambers include channels in which different cells are cultured, are arranged on the plate to be parallel to each other in one direction, and are arranged adjacent to each other such that at least some sections communicate with each other.

In the biomimetic chip according to an embodiment of the present disclosure, the plurality of chambers may include a first cell culture chamber including a first culture channel and in which first cells are cultured, a second cell culture chamber arranged on one side of the first cell culture chamber, including a second culture channel communicating with the first culture channel, and in which second cells are cultured, and a first culture medium chamber arranged on one side of the second cell culture chamber, including a first culture medium channel communicating with the second culture channel, and into which a culture medium is injected.

In the biomimetic chip according to an embodiment of the present disclosure, the first culture channel, the second culture channel, and the first culture medium channel may be formed into one body.

The biomimetic chip according to an embodiment of the present disclosure may further include a third cell culture chamber arranged on the other side of the first culture medium chamber to face the second cell culture chamber, including a third culture channel communicating with the first culture medium channel, and in which the second cells are cultured.

The biomimetic chip according to an embodiment of the present disclosure may further include a second culture medium chamber arranged on the other side of the first cell culture chamber to face the first culture medium chamber, including a second culture medium channel communicating with the first culture channel, and into which a culture medium is injected.

In the biomimetic chip according to an embodiment of the present disclosure, third cells may be injected into the first culture medium chamber after a first period has elapsed after the first cells and the second cells are injected into the first cell culture chamber and the second cell culture chamber, respectively.

In the biomimetic chip according to an embodiment of the present disclosure, the plurality of posts may include a plurality of first posts arranged at a first gap along a boundary between the first culture channel and the second culture channel, and a plurality of second posts arranged at a second gap along a boundary between the second culture channel and the first culture medium channel, and the second gap may be greater than the first gap.

In the biomimetic chip according to an embodiment of the present disclosure, the plurality of posts may include a polygonal prism shape including one outwardly curved surface.

In the biomimetic chip according to an embodiment of the present disclosure, the cell may be at least one of an endometrial epithelial cell, an endometrial stromal fibroblast, and a uterine vascular endothelial cell, which are specific cells of an endometrium.

An endometrium simulating method according to another embodiment of the present disclosure is a method of three-dimensionally simulating an endometrium by culturing different cells in a plurality of chambers, which are arranged parallel to each other in one direction and communicate with each other, and the method may include culturing first cells in a first cell culture chamber, culturing second cells in a second cell culture chamber, injecting a culture medium into a first culture medium chamber, and after a first period has elapsed, culturing third cells in the first culture medium chamber.

The endometrium simulating method according to another embodiment of the present disclosure may further include, before the injecting of the culture medium, culturing the second cells in a third cell culture chamber.

In the endometrium simulating method according to another embodiment of the present disclosure, the first cells may be uterine vascular endothelial cells, the second cells may be endometrial stromal fibroblasts, and the third cells may be endometrial epithelial cells.

In the endometrium simulating method according to another embodiment of the present disclosure, the first period may be a period during which the second cells perform self-assembly in the second cell culture chamber, and thus, blood vessels are formed in the first cell culture chamber.

Other aspects, features, and advantages than those described above will become clear from the following detailed description, claims, and drawings for carrying out the present disclosure.

Advantageous Effects

A three-dimensional biomimetic chip and an endometrium simulating method according to the present disclosure may three-dimensionally simulate an endometrium by culturing different cells in a plurality of chambers forming a multi-layered structure.

In addition, the three-dimensional biomimetic chip and the endometrium simulating method according to the present disclosure may provide a biomimetic chip having high biosimilarity to an endometrium by using specific cells of the endometrium (e.g., endometrial stromal fibroblasts, endometrial epithelial cells, and uterine vascular endothelial cells).

In addition, the three-dimensional biomimetic chip and the endometrium simulating method may provide a biomimetic chip that may be used for drug testing for treating various uterine diseases or for patient-specific treatment.

BEST MODE

Figure 1:
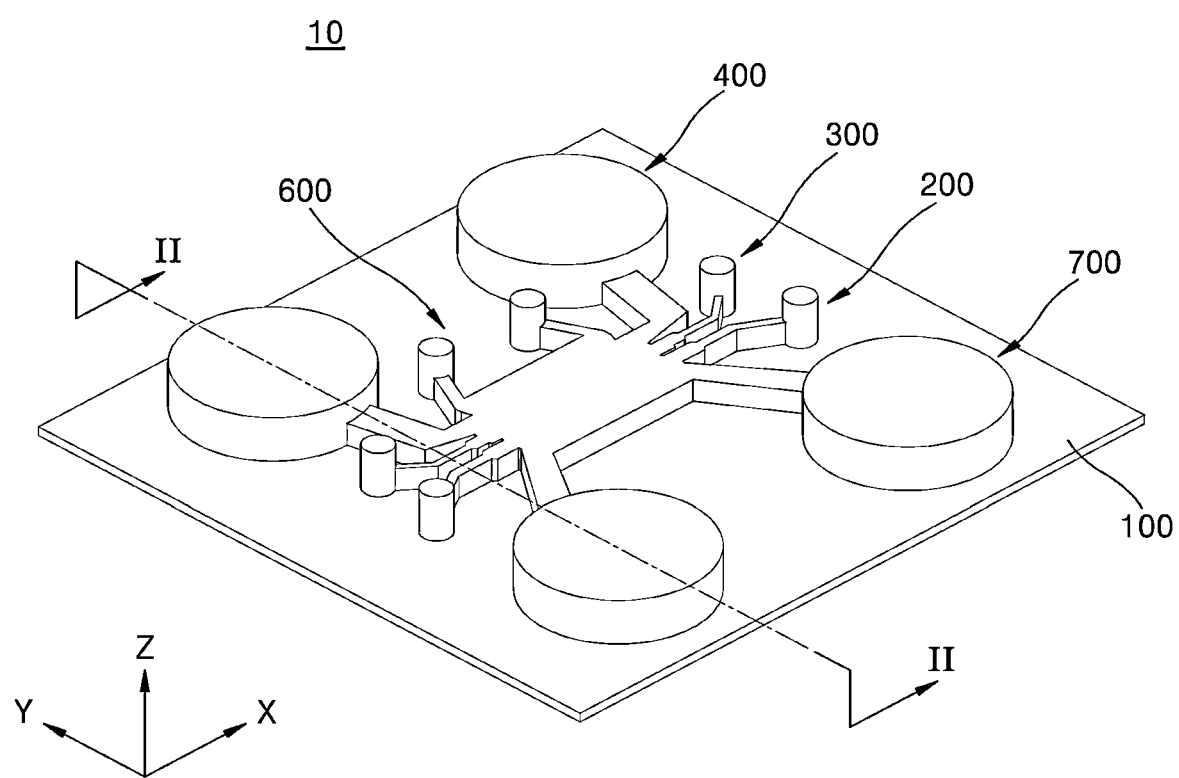
FIG. 1 illustrates a biomimetic chip for simulating an endometrium according to an embodiment of the present disclosure.

A biomimetic chip according to an embodiment of the present disclosure is a three-dimensional biomimetic chip including a plate, a plurality of chambers, and a plurality of posts, which are arranged between the plurality of chambers, wherein the plurality of chambers include channels in which different cells are cultured, are arranged on the plate to be parallel to each other in one direction, and are arranged adjacent to each other such that at least some sections communicate with each other.

MODE FOR INVENTION

As the present disclosure allows for various changes and numerous embodiments, particular embodiments will be illustrated in the drawings and described in detail. However, this is not intended to limit the present disclosure to particular modes of practice, and it is to be appreciated that all changes, equivalents, and substitutes that do not depart from the spirit and technical scope of the present disclosure are encompassed in the present disclosure. In describing the present disclosure, the same reference numerals are used for the same elements even when they are illustrated in different embodiments.

Terms such as 'first' or 'second' may be used to describe various elements, but the elements should not be limited by the terms. These terms are only used to distinguish one element from another element.

Terms used herein are for describing particular embodiments and are not intended to limit the scope of the present disclosure. As used herein, terms such as "comprises," "includes," or "has" specify the presence of stated features, numbers, stages, operations, components, parts, or a combination thereof, but do not preclude the presence or addition of one or more other features, numbers, stages, operations, components, parts, or a combination thereof.

Hereinafter, the present disclosure will be described in detail with reference to embodiments of the present disclosure illustrated in the accompanying drawings.

Figure 2:
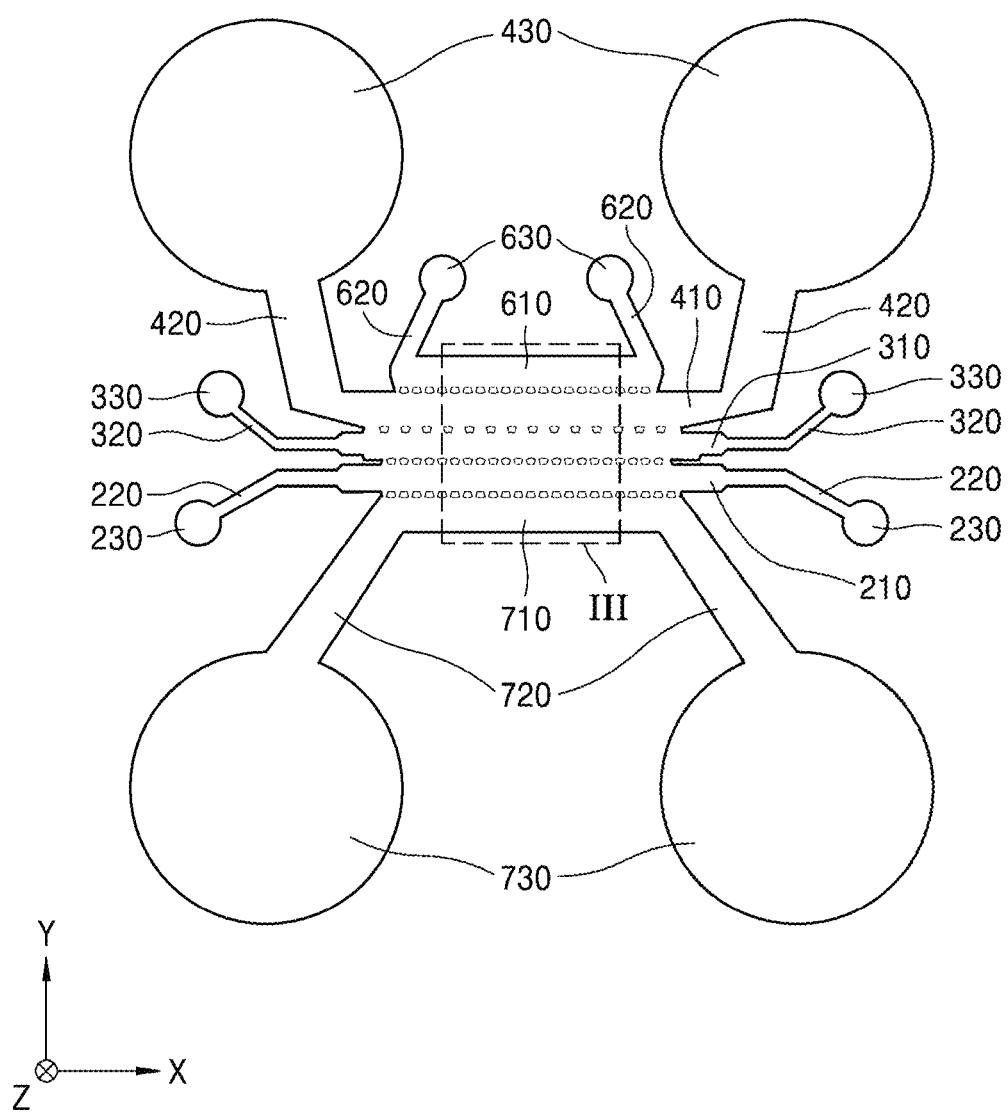
FIG. 2 illustrates a cross section taken along II-II in FIG. 1.
Figure 3:
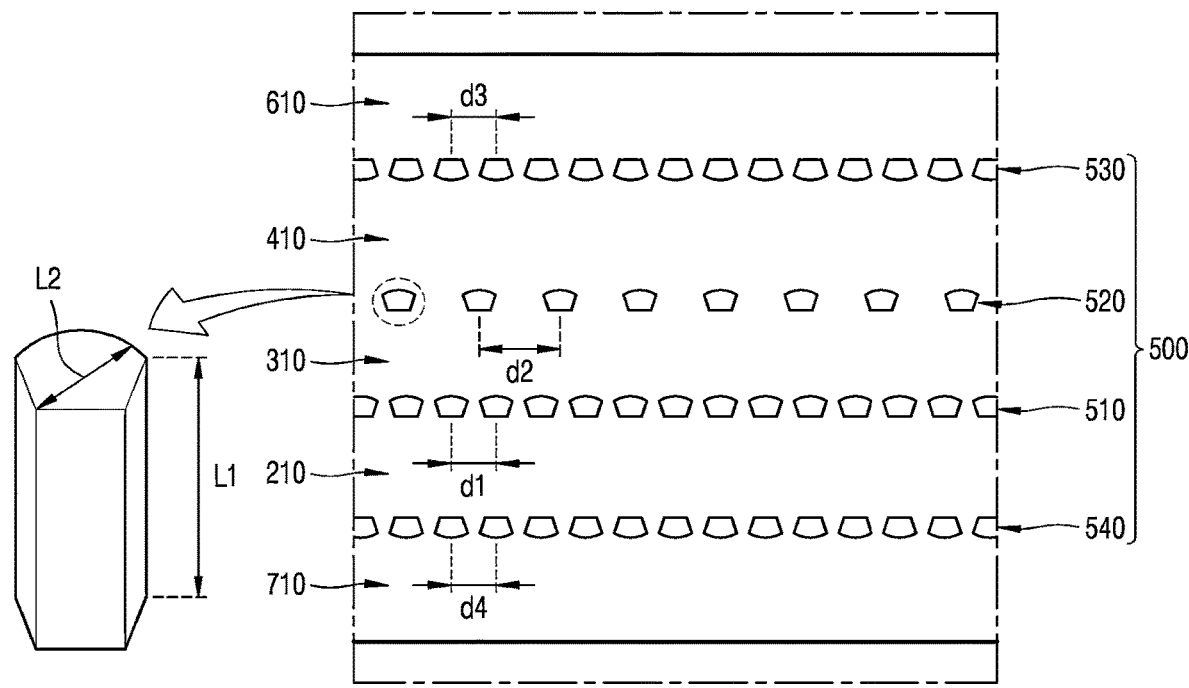
FIG. 3 is an enlarged view of III of FIG. 2.

FIG. 1 illustrates a biomimetic chip 10 for simulating an endometrium according to an embodiment of the present disclosure, FIG. 2 illustrates a cross section taken along II-II in FIG. 1, and FIG. 3 is an enlarged view of III of FIG. 2.

Referring to FIGS. 1 to 3, the biomimetic chip 10 according to an embodiment of the present disclosure may include a plate 100, a first cell culture chamber 200, a second cell culture chamber 300, and a first culture medium chamber 400.

The plate 100 includes an area in which chambers to be described below are arranged. The shape of the plate 100 is not particularly limited, and is sufficient to be a flat shape. In an embodiment, the plate 100 may be made of polydimethylsiloxane (PDMS), and may have a rectangular flat plate shape.

The first cell culture chamber 200 is a member in which cells are cultured, and is arranged on the plate 100.

The first cell culture chamber 200 may include a first culture channel 210, a first culture bridge 220, and a first cell inlet 230.

The first culture channel 210 may be arranged on the plate 100 in one direction (e.g., the X-axis direction of FIG. 1). The height of the first culture channel 210 is not particularly limited, but may be 250 μm to 300 μm for stable implantation of an embryo, as will be described below. First cells C1 may be cultured inside the first culture channel 210. This will be described below.

The first culture bridge 220 extends in a predetermined direction from an end of the first culture channel 210. In an embodiment, the first culture bridges 220 extend from both ends of the first culture channel 210, respectively. The direction in which the first culture bridge 220 extends is not particularly limited, but it is preferable that the first culture bridge 220 is sufficiently spaced from the second cell culture chamber 300 arranged adjacent to the first cell culture chamber 200.

In an embodiment, the width of the first culture bridge 220 may be less than the width of the first culture channel 210.

The first cell inlet 230 is connected to an end of the first culture bridge 220. In an embodiment, the first cell inlets 230 may be arranged at one end and the other end of the first culture channel 210, respectively, so as to be connected to the respective first culture bridges 220, and each of the first cell inlets 230 may include a through hole (not shown) into which the first cells C1 are injected. The injected first cells C1 may move into the first culture channel 210 through the first culture bridge 220.

The shape of the first cell inlet 230 is not particularly limited. In an embodiment, the first cell inlet 230 may have a cylindrical shape having a height greater than that of the first culture channel 210.

The second cell culture chamber 300 is a member in which cells are cultured, and may be arranged on one side of the first cell culture chamber 200 so as to be parallel to the first cell culture chamber 200 on the plate 100. In an embodiment, the second cell culture chamber 300 may be arranged adjacent to the first cell culture chamber 200 in the +Y-axis direction therefrom.

The second cell culture chamber 300 may include a second culture channel 310, a second culture bridge 320, and a second cell inlet 330.

The second culture channel 310 may be arranged on the plate 100 in one direction (e.g., the X-axis direction of FIG. 1). The height of the second culture channel 310 is not particularly limited, but may be equal to the height of the first culture channel 210. Second cells C2 may be cultured inside the second culture channel 310. In an embodiment, the second cells C2 may produce an angiogenesis-promoting factor. This will be described below.

The second culture channel 310 may communicate with the first culture channel 210. In an embodiment, as illustrated in FIG. 2, the boundary between the first culture channel 210 and the second culture channel 310 may be open, and a plurality of first posts 510 to be described below may be arranged along the boundary.

The second culture bridge 320 may extend in a predetermined direction from an end of the second culture channel 310. The second cell inlet 330 may be connected to the second culture bridge 320, and the second cells C2 may be injected through the second cell inlet 330. The injected second cells C2 may move into the second culture channel 310 through the second culture bridge 320.

The other configurations of the second culture bridge 320 and the second cell inlet 330 may be the same as those of the first culture bridge 220 and the first cell inlet 230, and detailed descriptions thereof will be omitted.

The first culture medium chamber 400 is a member into which a culture medium is injected, and may be arranged on one side of the second cell culture chamber 300 so as to be parallel to the first cell culture chamber 200 and/or the second cell culture chamber 300, on the plate 100. In an embodiment, the first culture medium chamber 400 may be arranged adjacent to the second cell culture chamber 300 in the +Y-axis direction therefrom.

The first culture medium chamber 400 may include a first culture medium channel 410, a first culture medium bridge 420, and a first culture medium inlet 430.

The first culture medium channel 410 may be arranged on the plate 100 in one direction (e.g., the X-axis direction of FIG. 1). The height of the first culture medium channel 410 is not particularly limited, but may be equal to the height of the first culture channel 210. Third cells C3 may be cultured inside the first culture medium channel 410. This will be described below.

The first culture medium channel 410 may communicate with the second culture channel 310. In an embodiment, as illustrated in FIG. 2, the boundary between the second culture channel 310 and the first culture medium channel 410 may be open, and a plurality of second posts 520 to be described below may be arranged along the boundary.

The first culture medium bridge 420 may extend in a predetermined direction from an end of the first culture medium channel 410. The first culture medium inlets 430 may be connected to the first culture medium bridges 420, respectively, and may be arranged at both ends of the first culture medium channel 410, respectively. The culture medium injected through the first culture medium inlet 430 may move into the first culture medium channel 410 through the first culture medium bridge 420.

In an embodiment, the first culture channel 210, the second culture channel 310, and the first culture medium channel 410 may be arranged adjacent to each other and parallel to each other in one direction.

Accordingly, in the biomimetic chip 10 according to an embodiment of the present disclosure, channels (chambers) in which different cells are cultured form a multi-layered structure in one direction, and thus, the biomimetic chip 10 may simulate a human body, particularly an endometrium, in a biocompatible manner.

In an embodiment, the first culture channel 210, the second culture channel 310, and the first culture medium channel 410 may form a common communication area. In more detail, as illustrated in FIG. 2, the boundaries between the first culture channel 210, the second culture channel 310, and the first culture medium channel 410 may be open to share at least a partial area therebetween.

Accordingly, the biomimetic chip 10 according to an embodiment of the present disclosure may allow different cells cultured in the respective channels (chambers) to be connected to each other, and thus implement a cell network. Therefore, there may be provided a biomimetic chip capable of three-dimensionally simulating an endometrium with improved biocompatibility compared to related-art two-dimensional biomimetic devices.

In an embodiment, the first cell culture chamber 200, the second cell culture chamber 300, and the first culture medium chamber 400 may constitute one body. In more detail, the first culture channel 210, the second culture channel 310, and the first culture medium channel 410 may be formed into an integral body, and the first culture bridge 220, the second culture bridge 320, and the first culture medium bridge 420 may be branched from the body in a predetermined direction.

Referring to FIGS. 2 and 3, the biomimetic chip 10 according to an embodiment of the present disclosure may further include posts 500.

A plurality of posts 500 may be arranged along the boundary between the chambers. In more detail, the plurality of posts 500 may be arranged at preset gaps between the first cell culture chamber 200 and the second cell culture chamber 300, and/or between the second cell culture chamber 300 and the first culture medium chamber 400. The posts 500 may be arranged at preset gaps to define the boundaries between the chambers, and thus set gaps or patterns of cells cultured in the chambers.

In an embodiment, an extracellular matrix may be arranged between the posts 500. Because the outer circumferential surface of the post 500 having a fine shape forms a kind of hydrophobic pattern, the extracellular matrix may exist in a spherical shape between the posts 500. In an embodiment, a hydrogel may be used as the extracellular matrix.

The posts 500 may include the first posts 510 and the second posts 520.

A plurality of first posts 510 may be arranged in one direction (e.g., the X-axis direction of FIG. 2) and along the boundary between the first cell culture chamber 200 and the second cell culture chamber 300. The shape of the first post 510 is not particularly limited, and may be a polygonal prism shape or a cylindrical shape. In an embodiment, as illustrated in the enlarged view of FIG. 3, the shape of the first post 510 may be a polygonal prism shape having one outwardly curved surface.

Accordingly, when cells are injected into the second cell culture chamber 300 and the biomimetic chip 10 is tilted, the cells may roll on the curved surfaces of the first posts 510 and thus be naturally positioned between the first posts 510.

The size of the first post 510 is not particularly limited. In an embodiment, a height L1 of the first post 510 may be equal to the heights of the first cell culture chamber 200 and the second cell culture chamber 300, and may be 250 μm to 300 μm. In addition, a maximum length L2 of the upper or lower surface of the first post 510 may be 180 μm to 200 μm.

A distance d1 between the first posts 510 is not particularly limited, and in an embodiment, the distance d1 may be equal to the length L2.

A plurality of second posts 520 may be arranged in one direction (e.g., the X-axis direction of FIG. 2) and along the boundary between the second cell culture chamber 300 and the first culture medium chamber 400. The size and shape of the second post 520 may be the same as or different from those of the first post 510.

Accordingly, as will be described below, when an embryo is injected through the first culture medium chamber 400 and the biomimetic chip 10 is tilted, the embryo may roll on the curved surfaces of the second posts 520 and thus be naturally positioned between the second posts 520.

In an embodiment, the distance d2 between the second posts 520 may be greater than the distance d1 between the first posts 510. In more detail, the distance d2 between the second posts 520 may be 180 μm to 200 μm. As will be described below, by increasing the distance between the second posts 520, embryos may be more stably implanted between the second posts 520.

Referring back to FIGS. 1 and 2, the biomimetic chip 10 according to an embodiment of the present disclosure may further include a third cell culture chamber 600 and a second culture medium chamber 700.

The third cell culture chamber 600 is a member in which cells are cultured, and may be arranged on one side of the first culture medium chamber 400 on the plate 100 so as to be parallel to the first culture medium chamber 400. In an embodiment, the third cell culture chamber 600 may be arranged adjacent to the first culture medium chamber 400 in the +Y-axis direction therefrom to face the second cell culture chamber 300 with the first culture medium chamber 400 therebetween.

In more detail, as illustrated in FIG. 2, the third cell culture chamber 600 may be arranged to be surrounded by the first culture medium chambers 400.

The third cell culture chamber 600 may include a third culture channel 610, a third culture bridge 620, and a third cell inlet 630.

The third culture channel 610 may be arranged on the plate 100 in one direction (e.g., the X-axis direction of FIG. 1). The height of the third culture channel 610 is not particularly limited, but may be equal to the height of the first culture channel 210. First cells C1 may be cultured inside the third culture channel 610. This will be described below.

The third culture channel 610 may communicate with the first culture medium channel 410. In an embodiment, as illustrated in FIG. 2, the boundary between the first culture medium channel 410 and the third culture channel 610 may be open, and a plurality of third posts 530 to be described below may be arranged along the boundary.

The third culture bridge 620 may extend in a predetermined direction from an end of the third culture channel 610. The third cell inlet 630 is connected to the third culture bridge 620, and the first cells C1 may be injected through the third cell inlet 630. The injected first cells C1 may move into the third culture channel 610 through the third culture bridge 620.

The other configurations of the third culture bridge 620 and the third cell inlet 630 may be the same as those of the first culture bridge 220 and the first cell inlet 230, and detailed descriptions thereof will be omitted.

The second culture medium chamber 700 is a member into which a culture medium is injected, and may be arranged on the other side of the first cell culture chamber

200 so as to be parallel to the first cell culture chamber 200 and/or the second cell culture chamber 300, on the plate 100. The culture medium injected into the second culture medium chamber 700 may be the same as the culture medium injected into the first culture medium chamber 400. In an embodiment, the second culture medium chamber 700 may be arranged adjacent to the first cell culture chamber 200 in the −Y-axis direction therefrom.

The second culture medium chamber 700 may include a second culture medium channel 710, a second culture medium bridge 720, and a second culture medium inlet 730.

The second culture medium channel 710 may be arranged on the plate 100 in one direction (e.g., X-axis direction of FIG. 1). The height of the second culture medium channel 710 is not particularly limited, but may be equal to the height of the first culture channel 210.

The second culture medium channel 710 may communicate with the first culture channel 210. In an embodiment, as illustrated in FIG. 2, the boundary between the first culture channel 210 and the second culture medium channel 710 may be open, and a plurality of fourth posts 540 to be described below may be arranged along the boundary.

The second culture medium bridge 720 may extend from an end of the second culture medium channel 710 in a predetermined direction. The second culture medium inlets 730 may be connected to the second culture medium bridges 720, respectively, and may be arranged at both ends of the second culture medium channel 710, respectively. The culture medium injected through the second culture medium inlet 730 may move into the second culture medium channel 710 through the second culture medium bridge 720.

In an embodiment, the first culture channel 210, the second culture channel 310, the first culture medium channel 410, the third culture channel 610, and the second culture medium channel 710 may be arranged parallel to each other in one direction.

In an embodiment, the first culture channel 210, the second culture channel 310, the first culture medium channel 410, the third culture channel 610, and the second culture medium channel 710 may form a common communication area. In more detail, as illustrated in FIG. 2, the boundaries between the first culture channel 210, the second culture channel 310, the first culture medium channel 410, the third culture channel 610, and the second culture medium channel 710 may be open to share at least a partial area.

In an embodiment, the first culture channel 210, the second culture channel 310, the first culture medium channel 410, the third culture channel 610, and the second culture medium channel 710 may constitute one body. In more detail, the first culture channel 210, the second culture channel 310, the first culture medium channel 410, the third culture channel 610, and the second culture medium channel 710 may be formed into an integral body and may be made of PDMS. In addition, each of the first culture bridge 220, the second culture bridge 320, the first culture medium bridge 420, the third culture bridge 620, and the second culture medium bridge 720 may be branched from the body in a predetermined direction.

In an embodiment, each of the first cell C1, the second cell C2, and the third cell C3 may be a specific cell of an endometrium. In more detail, the first cell C1 may be a uterine vascular endothelial cell, the second cell C2 may be an endometrial stromal fibroblast, and the third cell C3 may be an endometrial epithelial cell.

The second cells C2, which are endometrial stromal fibroblasts cultured in the second cell culture chamber 300, may produce angiogenesis-promoting factors. For example, the second cells C2 may produce a vascular endothelial growth factor (VEGF). The first cells C1, which are uterine vascular endothelial cells cultured in the first cell culture chamber 200, may be stimulated by the produced VEGF and thus form a blood vessel while performing self-assembly. In addition, other angiogenesis-promoting factors may include a direct angiogenic factor (DAF), which directly stimulates endothelial cells, and an indirect angiogenic factor (IAF), which induces angiogenesis through the production of a DAF by stimulating perivascular cells.

As described above, the first cell culture chamber 200 and the second cell culture chamber 300 are arranged parallel to each other in one direction. That is, the first cell culture chamber 200 and the second cell culture chamber 300 may form a multi-layered structure in one direction. Accordingly, the first cells C1 cultured in the first cell culture chamber 200 form blood vessels toward the second cell culture chamber 300 in which the second cells C2 are located.

Therefore, the biomimetic chip 10 according to an embodiment of the present disclosure may implement a biomimetic chip that is biologically similar to an endometrium by culturing specific cells of the endometrium in a multi-layered structure.

In addition, the biomimetic chip 10 according to an embodiment of the present disclosure may more reliably induce the direction in which blood vessels are formed, by additionally culturing the first cells C1, which are uterine vascular endothelial cells, in the third cell culture chamber 600. In more detail, VEGFs are produced from the first cells C1, which are cultured not only in the second cell culture chamber 300 but also in the third cell culture chamber 600. Accordingly, the orientation of the blood vessels formed by the first cells C1 may be more reliably controlled to face the +Y-axis direction.

In an embodiment, the third cells C3, which are endometrial epithelial cells, may be cultured in the first culture medium chamber 400. In more detail, the third cells C3 may be injected into the first culture medium chamber 400 when a first period has elapsed after the first cells C1 and the second cells C2 are cultured. The third cells C3 may be arranged on the second posts 520 or on hydrogels arranged between the second posts 520. Here, the first period may be a period during which the first cells C1 perform self-assembly such that blood vessels form a vascular network, and the formed vascular network crosses the boundary between the first culture channel 210 and the second culture channel 310, and grows in the second culture channel 310.

Accordingly, the biomimetic chip 10 according to an embodiment of the present disclosure may simulate an endometrium in multiple layers by using specific cells of the endometrium, such as uterine vascular endothelial cells, endometrial stromal fibroblasts, or endometrial epithelial cells.

In addition, the biomimetic chip 10 according to an embodiment of the present disclosure may simulate the endometrium in a highly biocompatible manner as described above, and thus easily and efficiently implant an embryo on the endometrial epithelial cells.

In addition, the biomimetic chip 10 according to an embodiment of the present disclosure may cause endometrial blood vessels to be formed in a preset direction without separate power by using a plurality of channels (chambers) forming a multi-layered structure and particular post shapes, and may form a natural flow by using gravity.

In an embodiment, the biomimetic chip 10 according to the present disclosure may further include the third posts 530 and the fourth posts 540.

A plurality of third posts 530 may be arranged along the boundary between the first culture medium chamber 400 and the third cell culture chamber 600, to be spaced apart from each other by a preset distance d3. In addition, a plurality of fourth posts 540 may be arranged along the boundary between the first cell culture chamber 200 and the second culture medium chamber 700, to be spaced apart from each other by a preset distance d4.

In an embodiment, as illustrated in FIG. 3, the third posts 530 may be arranged such that their curved surfaces face the curved surfaces of the second posts 520. Accordingly, as will be described below, when an embryo is injected into the first culture medium chamber 400, the embryo may roll on the curved surfaces of the second posts 520 and the third posts 530 and then be seated on a space between the second posts 520.

Hereinafter, an endometrium simulating method according to another embodiment of the present disclosure will be described with reference to the drawings.

Figure 4A:
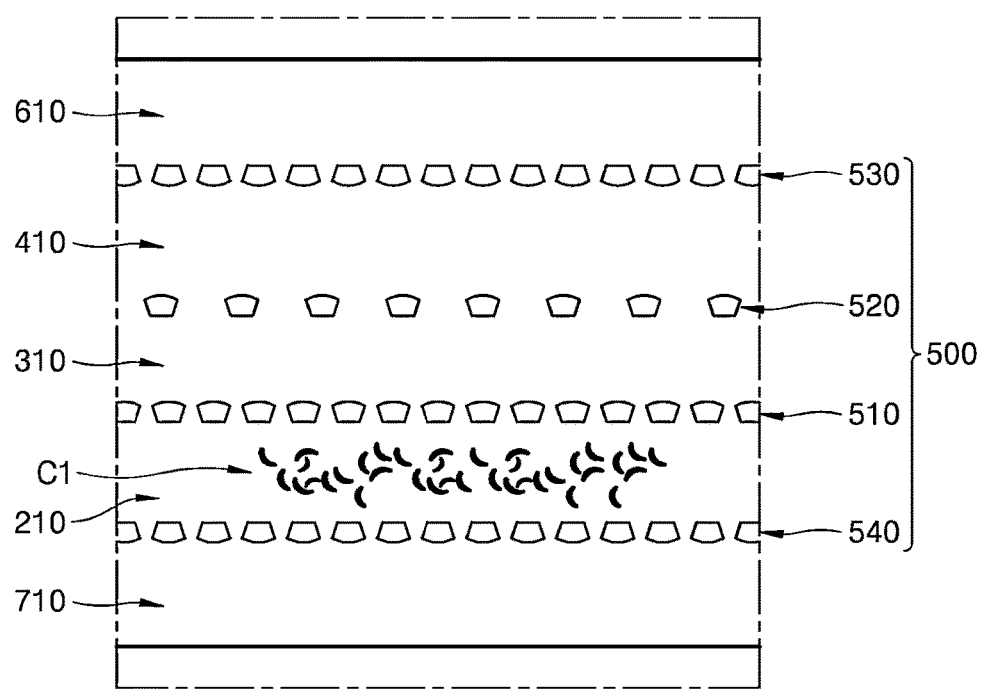
FIG. 4A illustrates a state in which first cells are injected into a first culture channel.
Figure 4B:
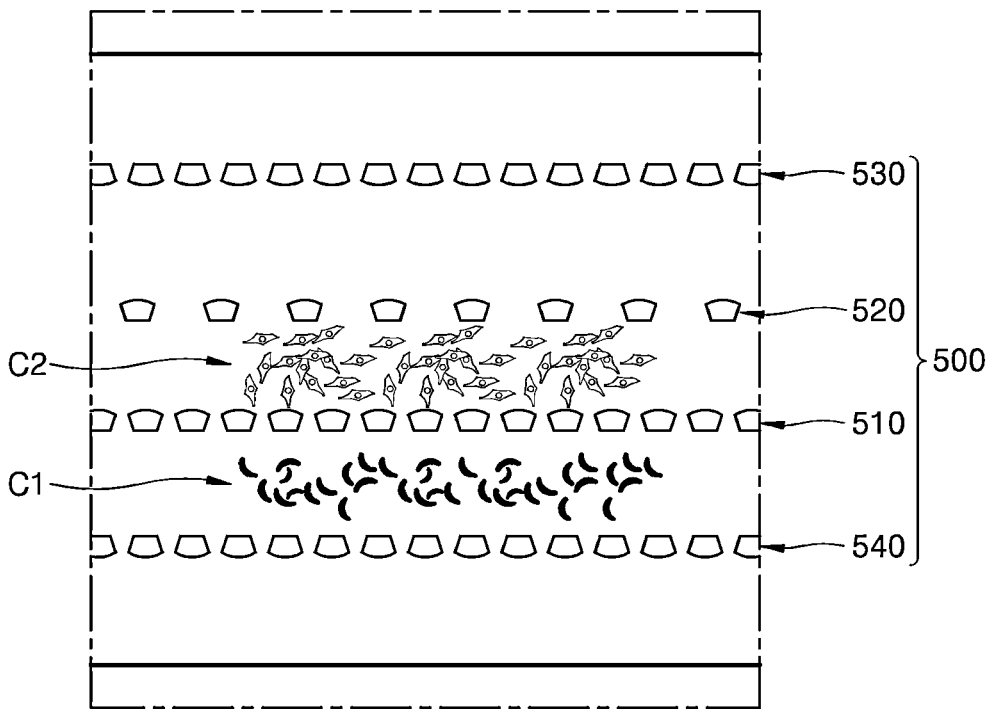
FIG. 4B illustrates a state in which second cells are injected into a second culture channel.
Figure 4C:
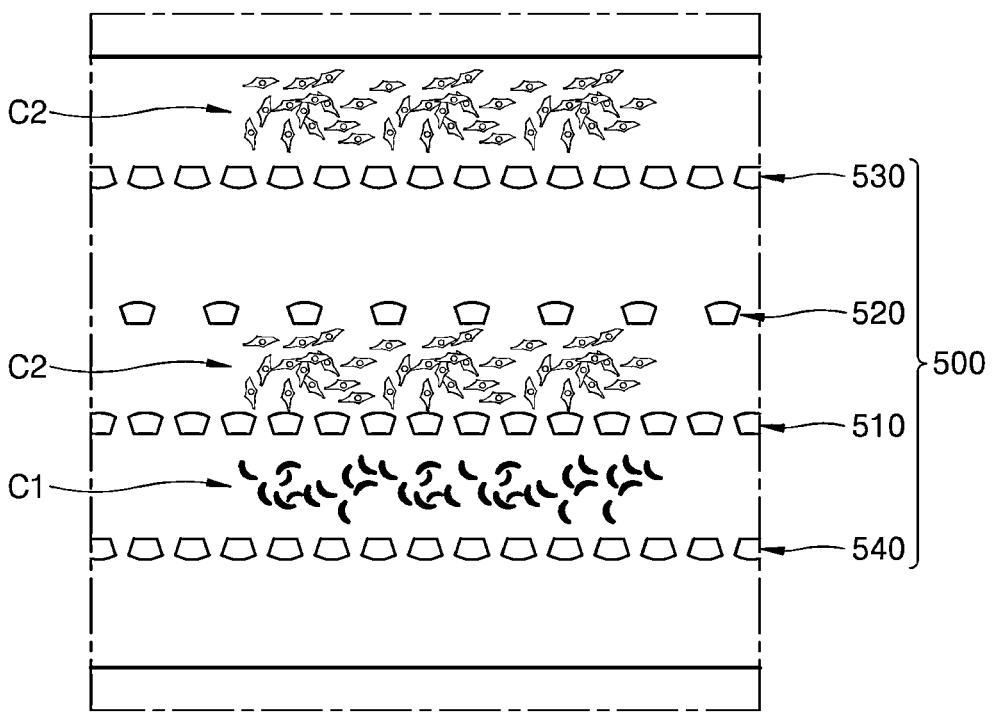
FIG. 4C illustrates a state in which second cells are injected into a third culture channel.
Figure 4D:
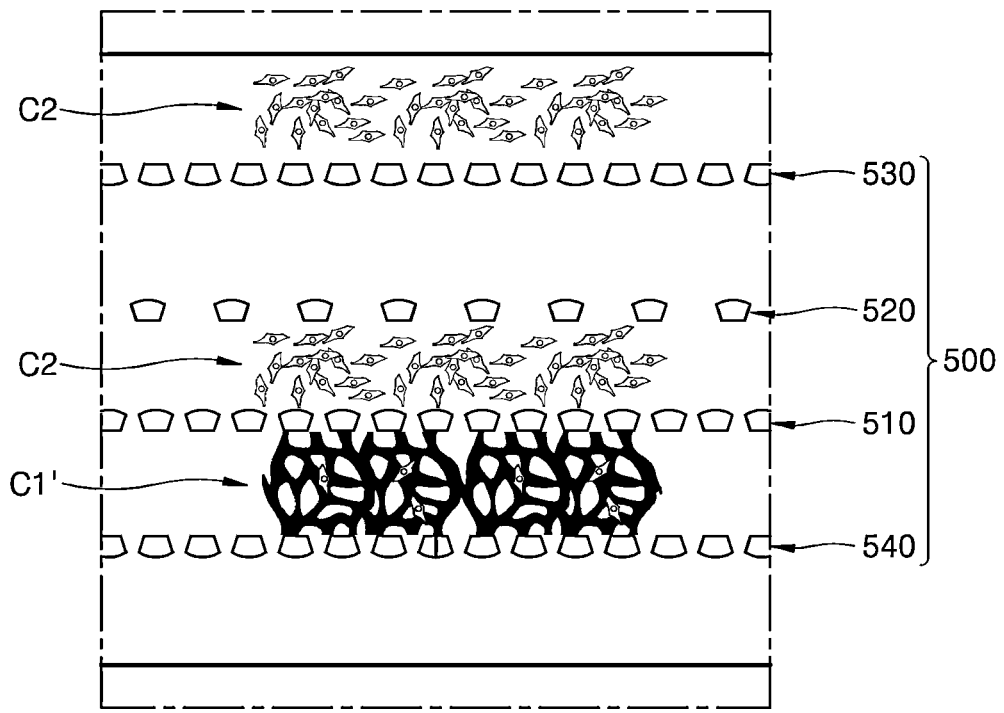
FIG. 4D illustrates a state in which first cells start to form blood vessels toward second cells.
Figure 4E:
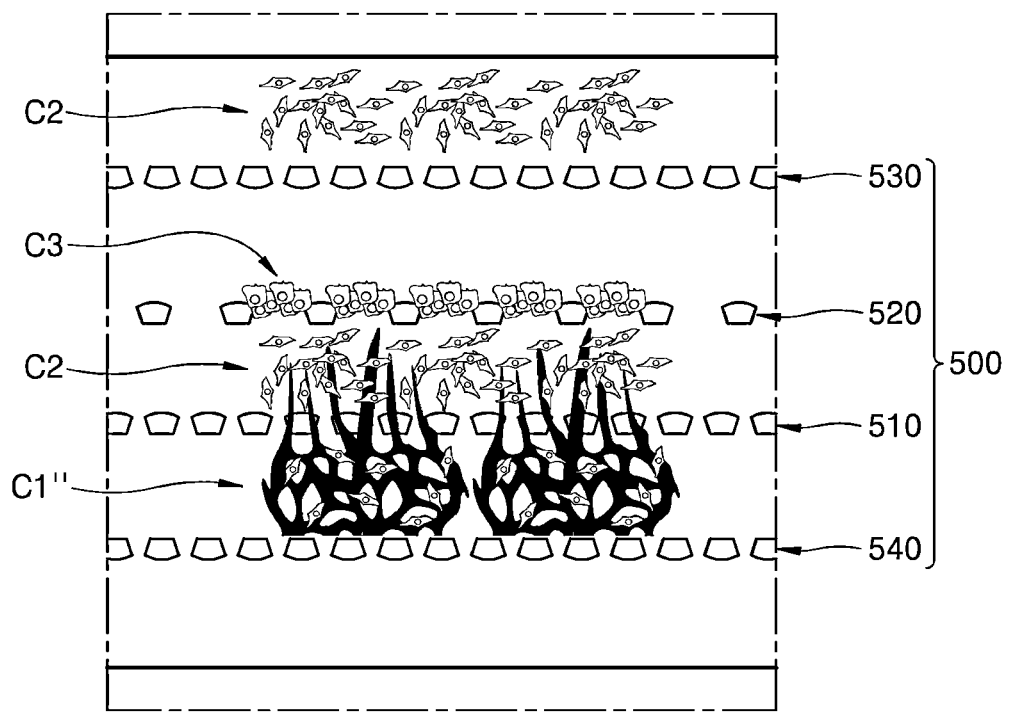
FIG. 4E illustrates a state in which blood vessels formed by first cells grow in a second culture channel and third cells are injected into a first culture medium channel.

FIG. 4A illustrates a state in which the first cells C1 are injected into the first culture channel 210, FIG. 4B illustrates a state in which the second cells C2 are injected into the second culture channel 310, FIG. 4C illustrates a state in which the second cells C2 are injected into the third culture channel 610, FIG. 4D illustrates a state in which the first cells C1 start to form blood vessels toward the second cells C2, and FIG. 4E illustrates a state in which the blood vessels formed by the first cells C1 grow in the second culture channel 310 and the third cells C3 are injected into the first culture medium channel 410.

The endometrium simulating method according to the present disclosure may three-dimensionally simulate an endometrium by using the biomimetic chip 10 to culture different cells in a plurality of chambers communicating with each other.

First, referring to FIGS. 1 to 4A, the first cells C1 are cultured in the first cell culture chamber 200, that is, the first culture channel 210. In a state in which the first cells C1 are inserted into a hydrogel, which is an extracellular matrix, the first cells C1 are injected through the first cell inlet 230 of the first cell culture chamber 200. In addition, the first cells C1 are moved to the first culture channel 210 by tilting the biomimetic chip 10 at an appropriate angle.

At this time, the first cells C1 that have been moved to the first culture channel 210 are arranged in a regular pattern while rolling on the plurality of fourth posts 540 spaced apart from each other by the preset distance d4. Accordingly, the first cells C1 may be patterned in the first culture channel 210.

In an embodiment, the first cells C1 may be uterine vascular endothelial cells, which are specific cells of an endometrium.

Next, the second cells C2 are cultured in the second cell culture chamber 300, that is, the second culture channel 310. Similarly, in a state in which the second cells C2 are inserted into a hydrogel, the second cells C2 are injected through the second cell inlet 330 of the second cell culture chamber 300. As the biomimetic chip 10 is tilted, the second cells C2 moves into the second culture channel 310.

Similarly, the second cells C2 that have been moved to the second culture channel 310 are arranged in a regular pattern while rolling on the plurality of first posts 510 spaced apart from each other by the preset distance d2. Accordingly, the second cells C2 may be patterned in the second culture channel 310.

In an embodiment, the second cells C2 may be endometrial stromal fibroblasts, which are specific cells of an endometrium.

However, the order of culturing the first cells C1 and the second cells C2 is not particularly limited, and the first cells C1 may be cultured after culturing the second cells C2, or the first cells C1 and the second cells C2 may be simultaneously cultured.

Next, a culture medium is injected into the first culture medium chamber 400. The culture medium injected through the first culture medium inlet 430 may be delivered to all of the chambers through spaces between the posts 500. At this time, a hydrogel as an extracellular matrix may be arranged between the posts 500, and the culture medium may diffuse through the hydrogel.

Accordingly, the first cells C1 may be cultured in the first cell culture chamber 200, and the second cells C2 may be cultured in the second cell culture chamber 300. As illustrated in FIG. 4D, the first cells C1 perform self-assembly to form a vascular network C1'. Then, as illustrated in FIG. 4E, as VEGFs are produced from the second cells C2, the vascular network C1' forms new blood vessels C1" toward the second cell culture chamber 300 in which the second cells C2 are located.

As such, the endometrium simulating method according to the present disclosure may simulate an endometrium in multiple layers by culturing different cells in a plurality of chambers arranged parallel to each other in one direction.

Next, after the first period has elapsed, the third cells C3 are cultured in the first culture medium chamber 400. After the third cells C3 are injected through the first culture medium chamber 400, the biomimetic chip 10 is tilted to roll the third cells C3. The third cells C3 naturally roll by gravity to be attached to the second posts 520 or the extracellular matrix arranged between the second posts 520.

In an embodiment, the first period may be a period during which the first cells C1 perform self-assembly to form the vascular network C1', and new blood vessels are formed in the second culture channel 310 in which the second cells C2 are located.

In an embodiment, the third cells C3 may be endometrial epithelial cells, which are specific cells of an endometrium.

As described above, the endometrium simulating method according to the present disclosure may simulate a real uterus in a biocompatible manner by culturing specific cells of an endometrium, such as uterine vascular endothelial cells, endometrial stromal fibroblasts, or endometrial epithelial cells, in a multi-layered structure.

In an embodiment, the endometrium simulating method may further include culturing the second cells C2 in the third cell culture chamber 600. In more detail, the first cells C1 and the second cells C2 are cultured in the first cell culture chamber 200 and the second cell culture chamber 300, respectively, and then, the second cells C2 are cultured in the third cell culture chamber 600 before injecting the culture medium. After injecting the second cells C2 through the third cell inlet 630 of the third cell culture chamber 600, the biomimetic chip 10 is tilted at an appropriate angle to move the second cells C2 to the third culture channel 610 (see FIG. 4C).

At this time, the second cells C2 that have been moved to the third culture channel 610 are arranged in a regular pattern while rolling on the plurality of third posts 530 spaced apart from each other by the preset distance d3. Accordingly, the second cells C2 may be patterned in the third culture channel 610.

As described above, in the endometrium simulating method according to the present disclosure, the second cells C2, which are endometrial stromal fibroblasts, may be arranged in multiple layers. Therefore, the absolute amount of VEGFs produced by the second cells C2 increases to promote the formation of blood vessels by the first cells C1, and impart directionality to the blood vessels to grow in one direction (e.g., the upward direction in FIG. 4E).

Figure 5:
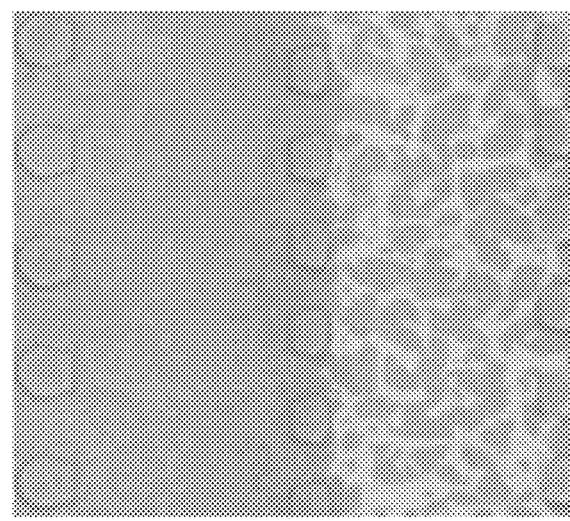
FIG. 5 shows a state in which first cells form blood vessels.
Figure 5:
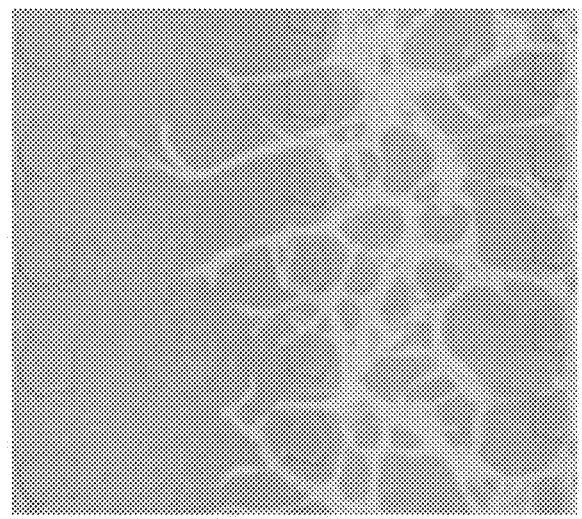
Figure 5:
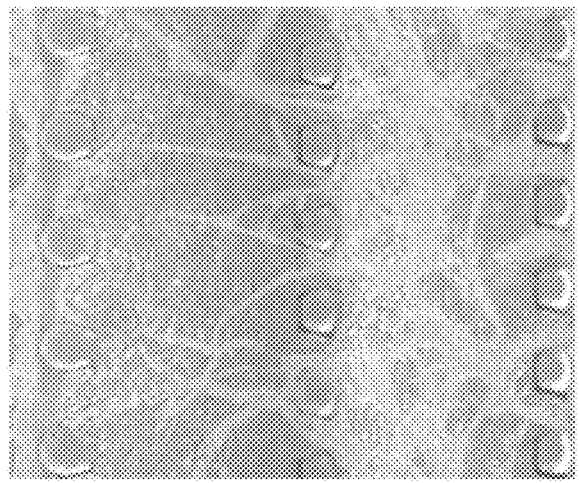
Figure 6:
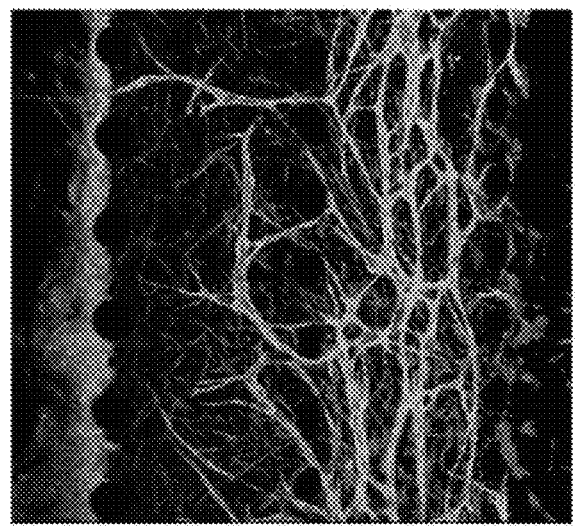
FIG. 6 shows a state of first cells according to a combination of a first cell culture chamber, a second cell culture chamber, and a third cell culture chamber.
Figure 6:
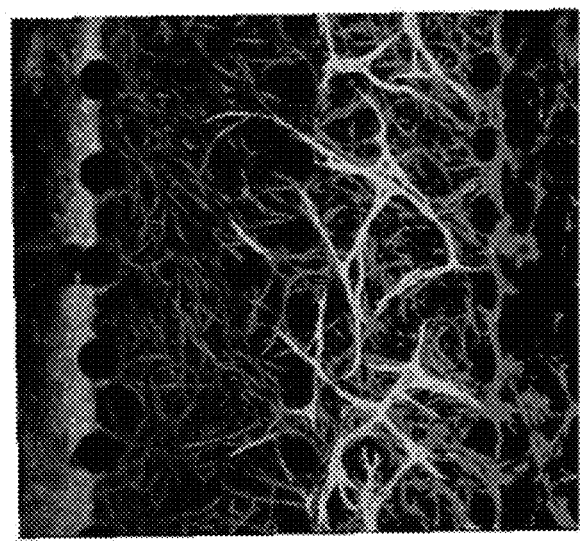
Figure 6:
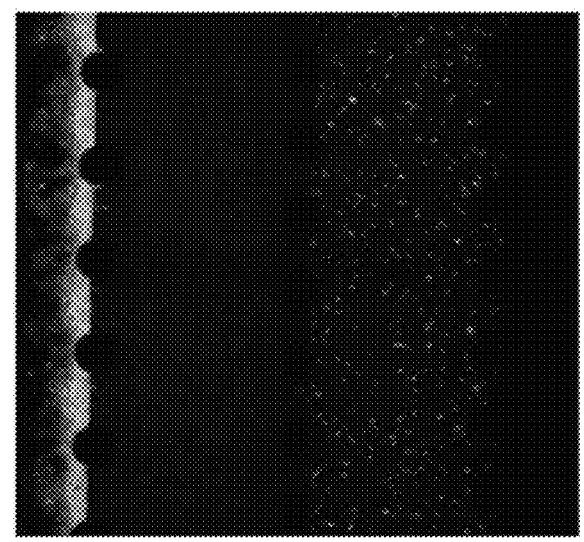
Figure 7A:
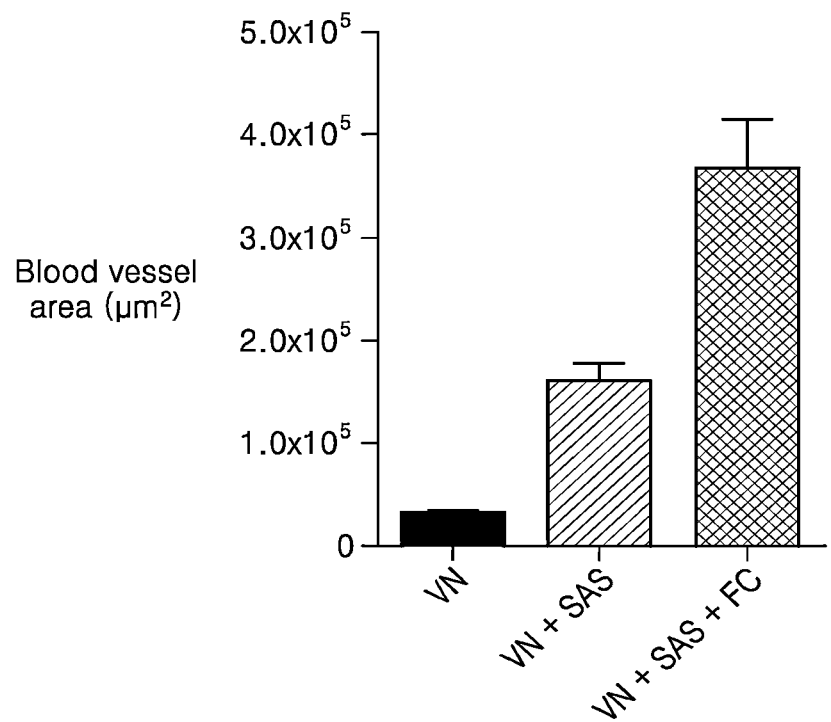
FIG. 7A shows a blood vessel area of a first cell culture chamber in the state shown in FIG. 6.
Figure 7B:
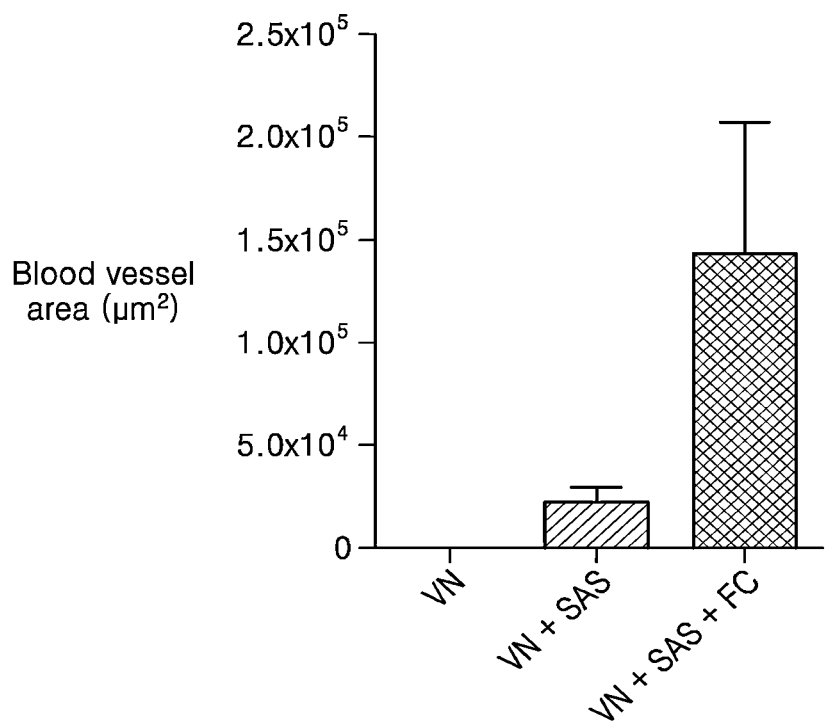
FIG. 7B shows a blood vessel area of a second cell culture chamber in the state shown in FIG. 6.

FIG. 5 shows a state in which the first cells C1 form blood vessels, FIG. 6 shows a state of the first cells C1 according to a combination of the first cell culture chamber 200, the second cell culture chamber 300, and the third cell culture chamber 600, FIG. 7A shows the blood vessel area of the first cell culture chamber 200 in the state shown in FIG. 6, and FIG. 7B shows the blood vessel area of the second cell culture chamber 300 in the state shown in FIG. 6.

Figure 8:
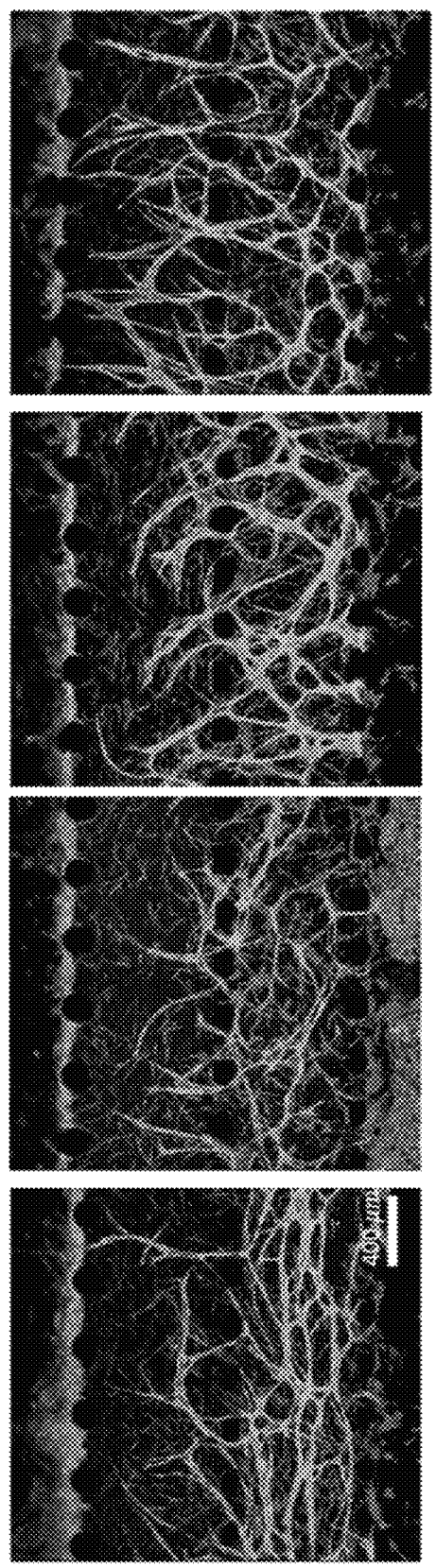
FIG. 8 shows a state of angiogenesis according to angiogenic factors.
Figure 9A:
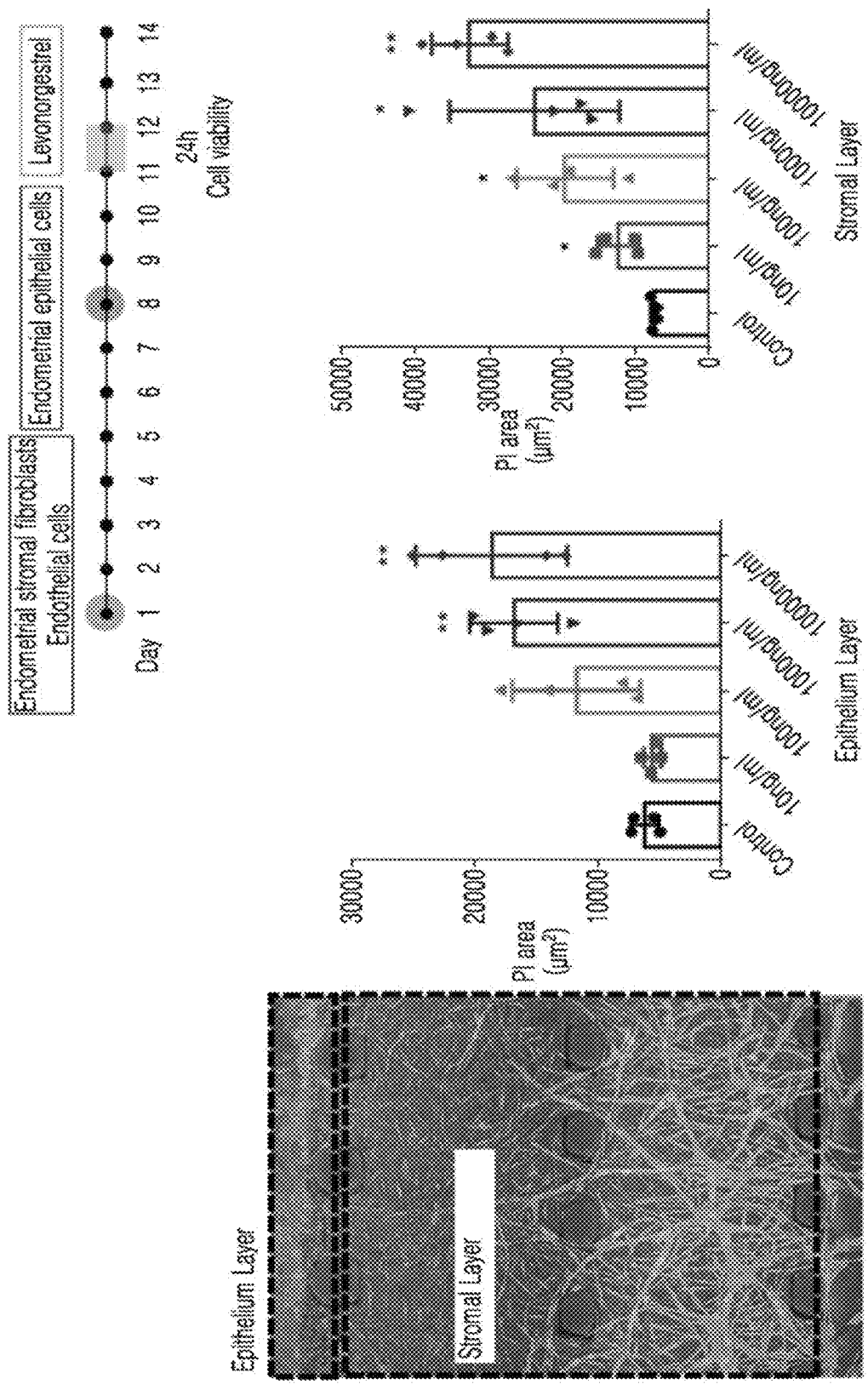
FIGS. 9A and 9B show results of cell viability experiments and blood vessel regression experiments using a biomimetic chip according to an embodiment of the present disclosure.
Figure 9B:
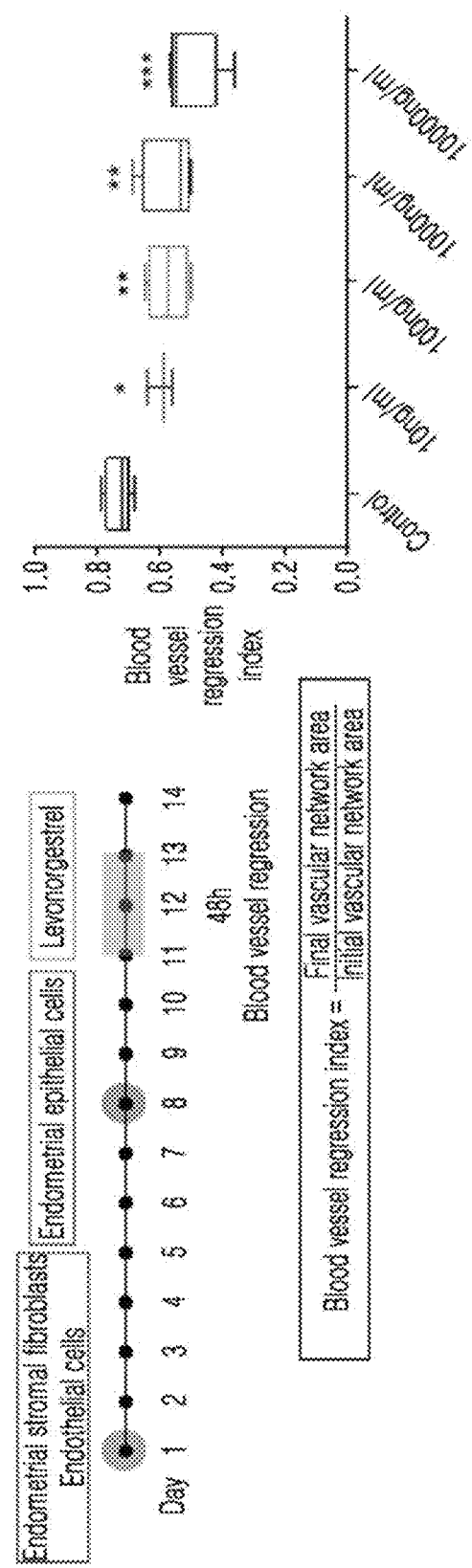
Figure 10A:
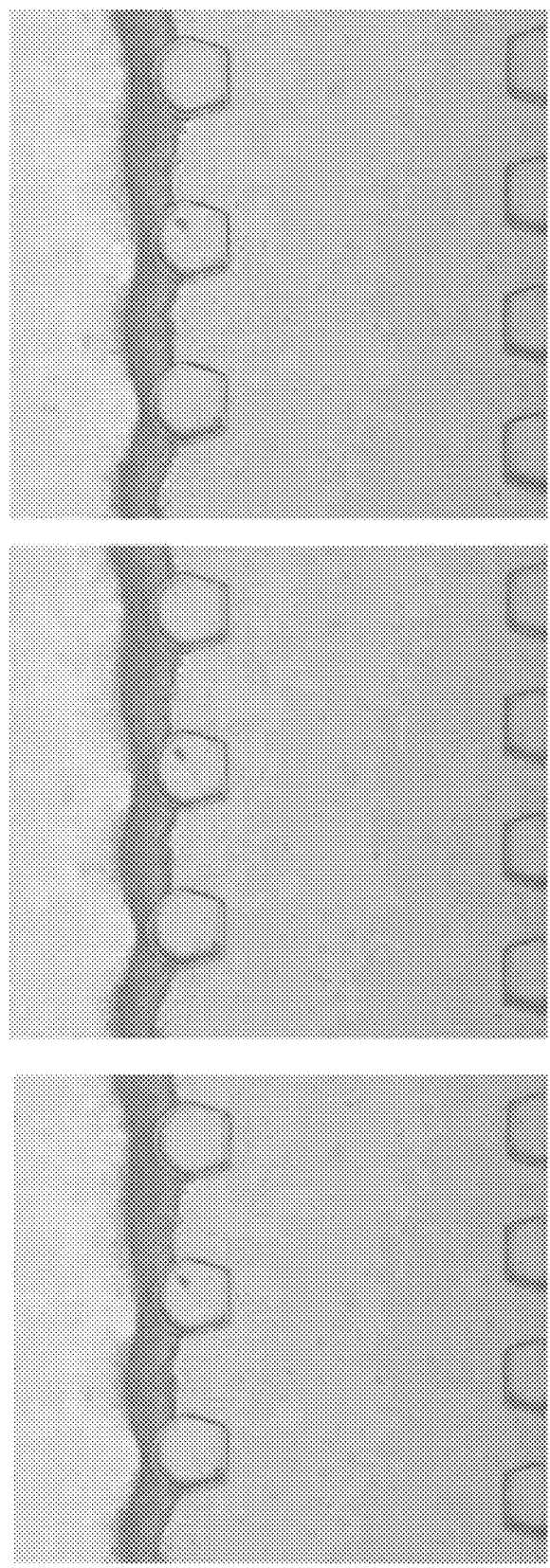
FIG. 10A shows a comparative example showing a permeability test of endometrial epithelial cells.
Figure 10B:
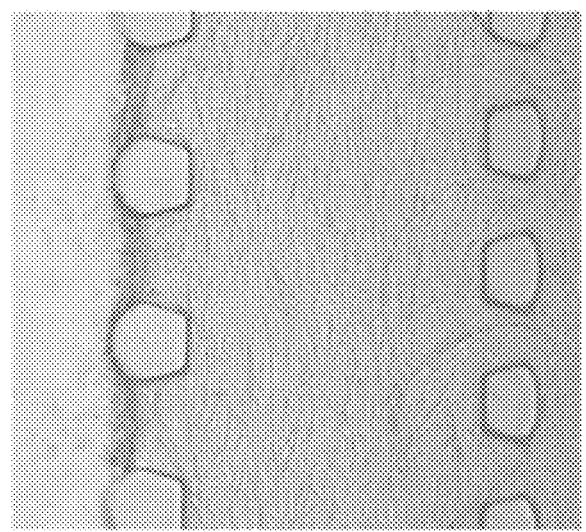
FIG. 10B shows an inventive example showing a permeability test of endometrial epithelial cells.
Figure 10B:
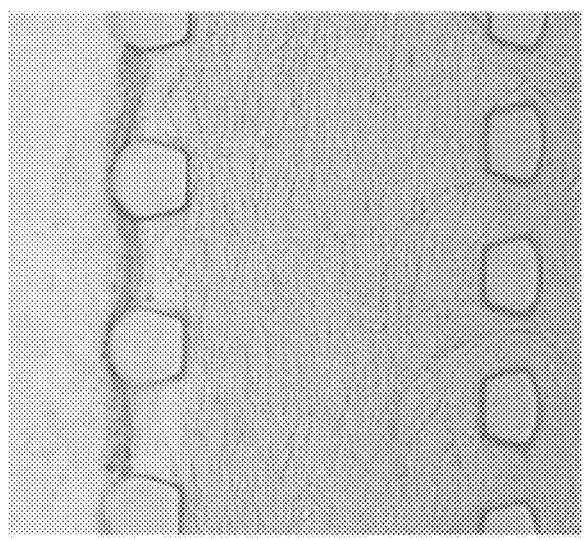
Figure 10B:
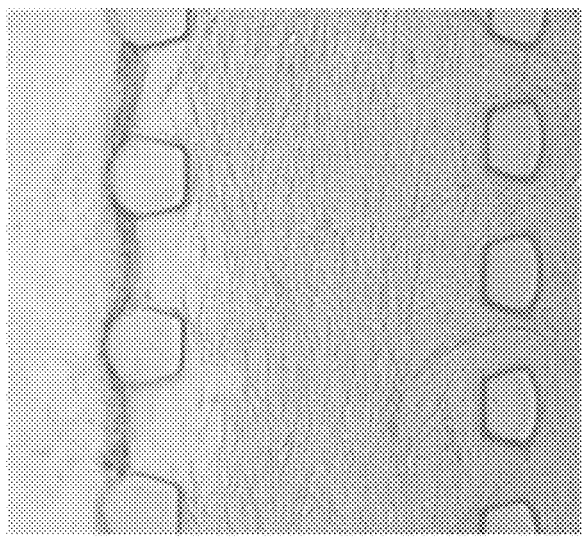
Figure 11A:
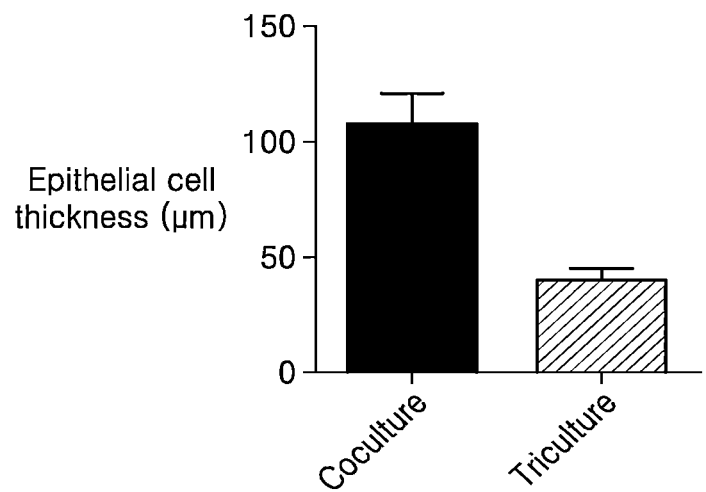
FIG. 11A shows the thickness of the endometrial epithelial cells of the comparative example and the inventive example.
Figure 11B:
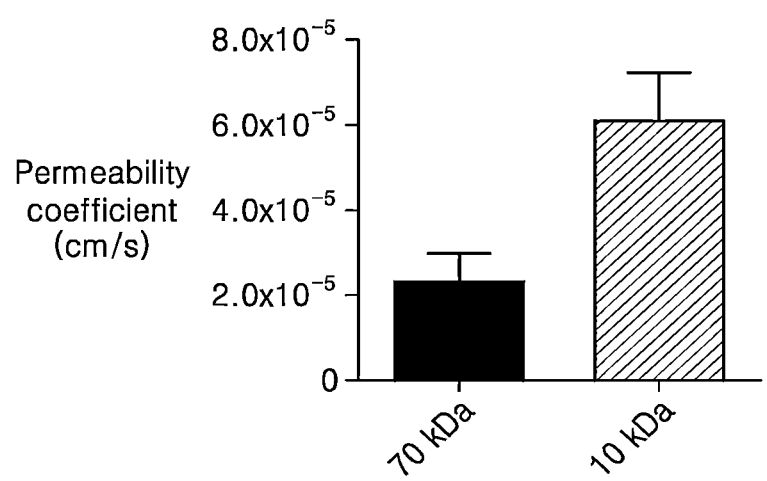
FIG. 11B shows the permeability of the inventive example.
Figure 12:
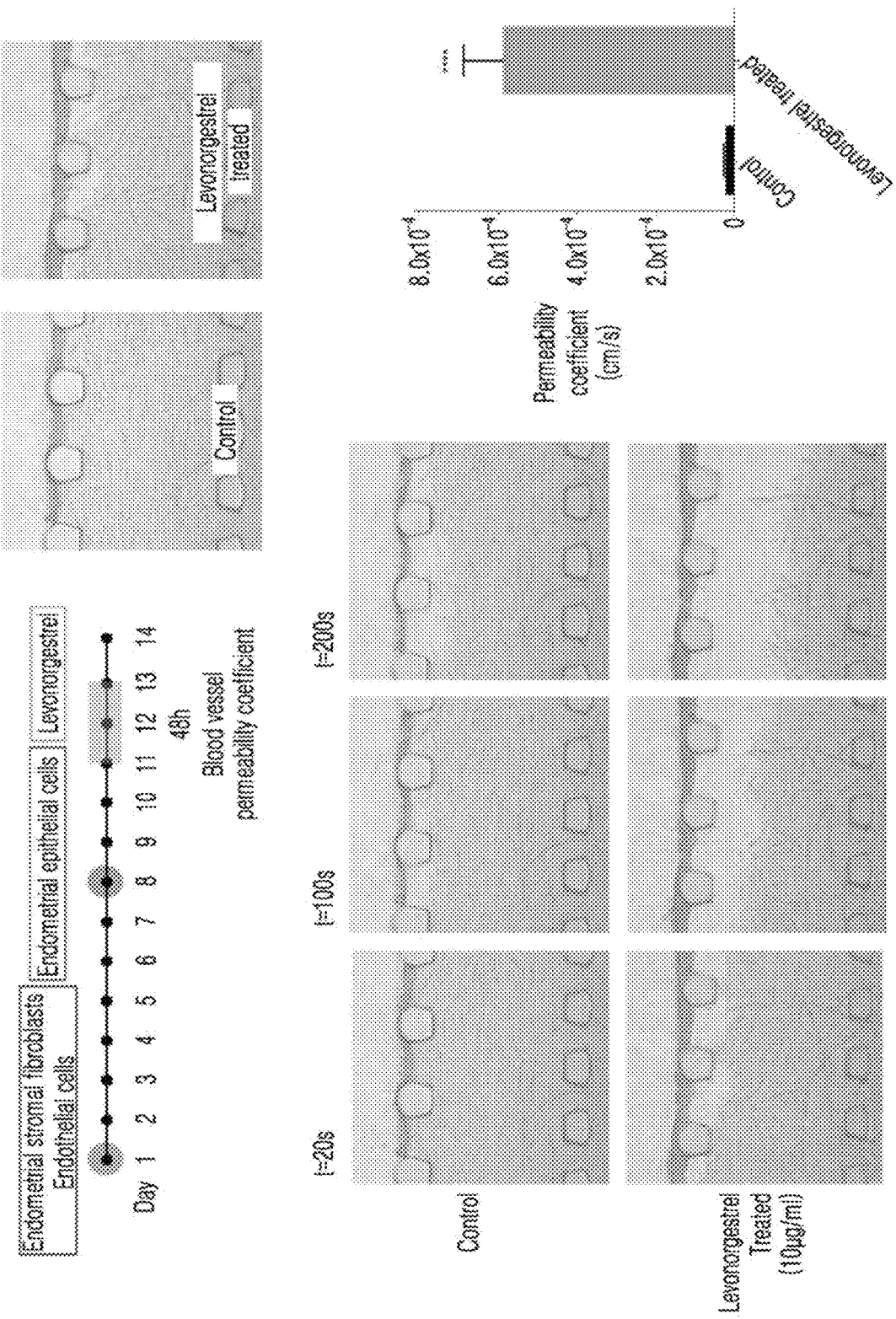
FIG. 12 shows a blood vessel permeability state of a fluorescent material according to drug treatment.
Figure 13:
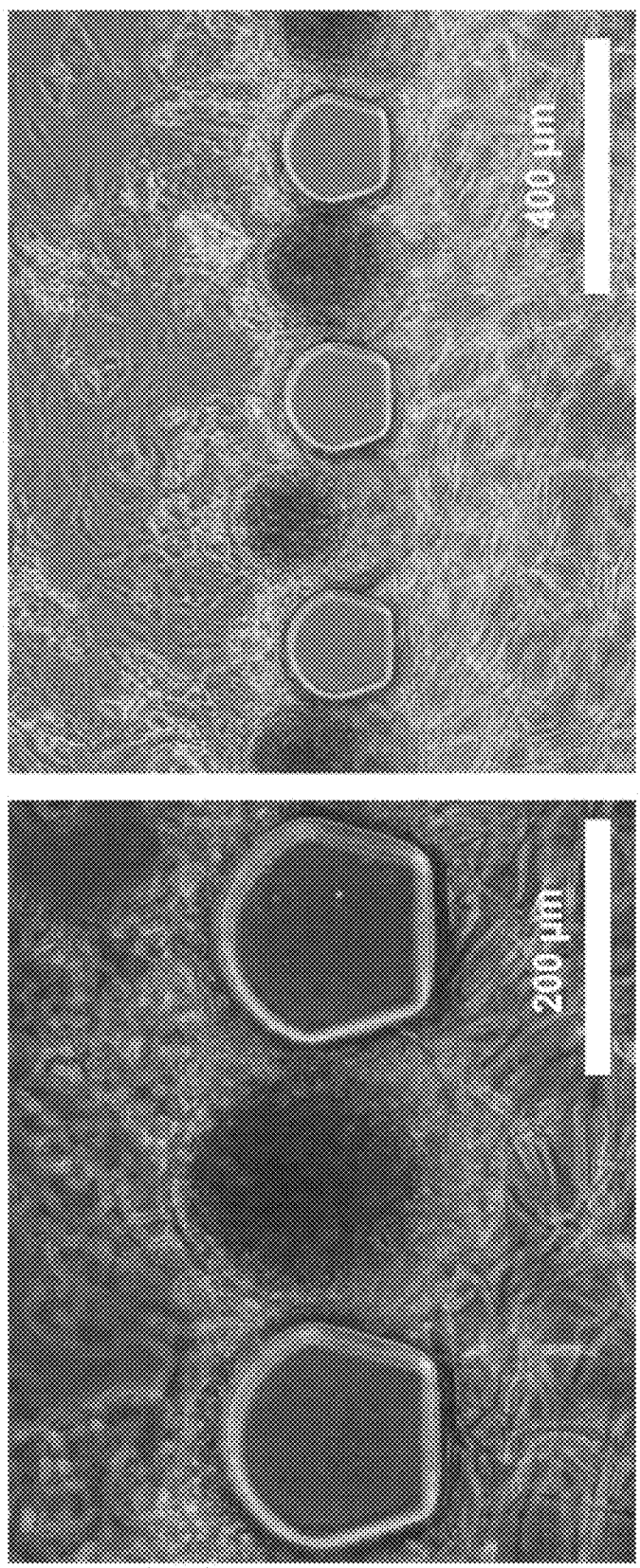
FIG. 13 shows an embryo implantation test using the present disclosure.

In addition, FIG. 8 shows a state of angiogenesis according to angiogenic factors, FIGS. 9A and 9B show results of cell viability experiments and blood vessel regression experiments using a biomimetic chip according to an embodiment of the present disclosure, FIG. 10A shows a comparative example showing a permeability test of endometrial epithelial cells, FIG. 10B shows an inventive example showing a permeability test of endometrial epithelial cells, FIG. 11A shows the thickness of the endometrial epithelial cells of the comparative example and the inventive example, FIG. 11B shows the permeability of the inventive example, FIG. 12 shows a blood vessel permeability state of a fluorescent material according to drug treatment, and FIG. 13 shows an embryo implantation test using the present disclosure.

In the biomimetic chip 10 according to the present disclosure, endometrial epithelial cells, endometrial stromal fibroblasts, and uterine vascular endothelial cells, which are specific cells of an endometrium, are arranged in multiple layers to simulate the properties of endometrial tissue.

Accordingly, the biomimetic chip 10 according to the present disclosure may check the state of cells cultured in each chamber and monitor quantitative and qualitative responses of the cells to a drug in real time.

In more detail, (a) to (c) of FIG. 5 show a state of simulating an endometrium by the biomimetic chip 10 over time, wherein (a) shows Day 1, (b) shows Day 6, and (c) shows Day 8.

On Day 1, it may be seen that the first cells C1, which are uterine vascular endothelial cells, are cultured in the first cell culture chamber 200. On Day 6, it may be seen that, after the second cells C2, which are endometrial stromal fibroblasts, are cultured in the second cell culture chamber 300 and/or the third cell culture chamber 600, the first cells C1 performs self-assembly to form a vascular network. Then, on Day 8, it may be seen that that the third cells C3, which are endometrial epithelial cells, are cultured in the first culture medium chamber 400, and new blood vessels originating from the first cells C1 grow in the second cell culture chamber 300.

In addition, (a) of FIG. 6 shows a case in which only the first cells C1 are arranged in the first cell culture chamber 200, (b) of FIG. 6 shows a case in which the second cells C2 are additionally arranged in the second cell culture chamber 300, and (c) of FIG. 6 shows a case in which the second cells C2 are further arranged in the third cell culture chamber 600.

As may be seen in FIGS. 6, 7A, and 7B, it may be seen that, in the case in which only the first cells C1 are arranged in the first cell culture chamber 200, the blood vessel area of the first cell culture chamber 200 is significantly small compared to the other cases, and, in particular, no blood vessels grow at all in the second cell culture chamber 300. On the other hand, in the case in which the second cells C2 are cultured in each of the second cell culture chamber 300 and the third cell culture chamber 600, the VEGFs produced by the second cells C2 cause the blood vessel areas in the first cell culture chamber 200 and the second cell culture chamber 300 to be significantly large, and the blood vessels are formed in a distinct direction toward the second cells C2.

In addition, (a) to (d) of FIG. 8 show states in which different vascular inducing factors are injected into the biomimetic chip 10, wherein (a) of FIG. 8 shows a state in which no vascular inducing factor is injected, (b) of FIG. 8 shows a state in which sphingosine-1-phosphate (S1P) having an angiogenic effect is injected as a vascular inducing factor, (c) of FIG. 8 shows a state in which a VEGF, i.e., a vascular endothelial growth factor, is injected as a vascular inducing factor, and (d) of FIG. 8 shows a state in which both S1P and VEGF are injected.

As such, the biomimetic chip 10 according to the present disclosure may visually and in real time check the growth state of blood vessels, such as the area, length, and orientation, according to the injection state of each vascular inducing factor.

FIGS. 9A and 9B show results of cell viability experiments and blood vessel regression experiments on the first culture medium chamber 400 (Epithelium Layer in FIG. 9A) in which the third cells C3 were cultured, and the second cell culture chamber 300 (Stromal Layer in FIG. 9A) in which the second cells C2 were cultured, when a drug (levonorgestrel, which is an emergency contraceptive) was injected in different amounts (drug-untreated (Control), 10 ng/ml, 100 ng/ml, 1000 ng/ml, 10000 ng/ml), into the biomimetic chip 10 according to an embodiment of the present disclosure.

FIG. 10A shows, as the comparative example, a state in which only endometrial epithelial cells and uterine vascular endothelial cells are cultured. (a) to (c) of FIG. 10A show the states at time points when 20 seconds, 100 seconds, and 200 seconds have respectively elapsed after administration of FITC-dextran, which is a fluorescent material, and it may be seen that the endometrial epithelial cells are too thick (see FIG. 11A), such that the fluorescent material does not properly penetrate the endometrial epithelial cells. Accordingly, in the case in which only the endometrial epithelial cells and the uterine vascular endothelial cells were cultured, it was unable to measure the permeability of the endometrium.

On the other hand, FIG. 10B shows, as the inventive example, a state in which endometrial epithelial cells, endometrial stromal fibroblasts, and uterine vascular endothelial cells are all cultured. (a) to (c) of FIG. 10B show the states at time points when 20 seconds, 100 seconds, and 200 seconds have respectively elapsed after administration of FITC-dextran, and it may be seen that the endometrial epithelial cells are relatively thin (see FIG. 11A). Accordingly, in the case in which the endometrial epithelial cells, the endometrial stromal fibroblasts, and the uterine vascular endothelial cells were all cultured as in the present disclosure, it was able to measure the permeability of the endometrium.

FIG. 116 shows a result of calculating the permeability coefficient of an endometrium in the biomimetic chip 10 according to the present disclosure by using 70-kDa and 10-kDa fluorescent materials (FITC-dextran), respectively.

The permeability coefficient of the endometrium may be calculated according to the equation below.

$$P = \frac{1}{I_W} \times \frac{dI/dt}{I_J}$$

In the equation, $I_W$ denotes the thickness of the endometrial epithelial cell, $I_J$ denotes the average brightness outside the endometrial epithelial cell, and I denotes the brightness of the inner space of the endometrial epithelial cell, that is, the endometrial space.

As such, the biomimetic chip 10 according to the present disclosure simulates a state biocompatible with an endometrium, such that the reactivity of the endometrium to various drugs may be tested. In addition, the biomimetic chip 10 according to the present disclosure may measure the permeability of endometrial epithelial cells. Furthermore, based on this, the permeability of the endometrial epithelial cells according to administration of a contraceptive may be quantitatively measured.

FIG. 12 shows a permeability state of a fluorescent material according to drug treatment. In more detail, FIG. 12 shows the permeability state of the fluorescent material at time points (20 seconds, 100 seconds, and 200 seconds) after the fluorescent material is injected, in a case in which no drug treatment is performed (Control) and a case in which drug treatment using an emergency contraceptive is performed (10 µg/ml).

As shown in FIG. 12, it may be seen that the permeation of the fluorescent material is relatively slow in the case in which no treatment is performed, whereas the permeation of the fluorescent material is relatively fast in the case in which the drug treatment is performed. In addition, it may be seen that the permeability of the fluorescent material in the case in which the drug treatment is performed is much greater than that in the case in which no drug treatment is performed.

(a) and (b) of FIG. 13 show states in which embryos (beads as artificial embryos) are implanted in the first culture medium chamber 400.

In more detail, the embryos are injected in a state in which endometrial epithelial cells, endometrial stromal fibroblasts, and uterine vascular endothelial cells are cultured in the biomimetic chip 10. The embryos may be injected through the first culture medium chamber 400. In addition, the biomimetic chip 10 is vertically erected such that the injected embryos may be naturally implanted by gravity, and then culture is performed.

As described above, the plurality of second posts 520 are arranged to be spaced apart from each other by the preset distance d2 on the boundary between the second cell culture chamber 300 and the first culture medium chamber 400, and endometrial epithelial cells are cultured around the plurality of second posts 520. In particular, the second posts 520 of the biomimetic chip 10 according to the present disclosure are arranged to be spaced apart from each other by a distance greater than that in the related-art biomimetic devices. Accordingly, embryos may be naturally arranged between the second posts 520 while rolling along the curved surfaces of the second posts 520.

A three-dimensional biomimetic chip and an endometrium simulating method according to the present disclosure may three-dimensionally simulate an endometrium by culturing different cells in a plurality of chambers forming a multi-layered structure.

In addition, the three-dimensional biomimetic chip and the endometrium simulating method according to the present disclosure may provide a biomimetic chip having high biosimilarity to an endometrium by using specific cells of the endometrium (e.g., endometrial stromal fibroblasts, endometrial epithelial cells, and uterine vascular endothelial cells).

In addition, the three-dimensional biomimetic chip and the endometrium simulating method according to the present disclosure may provide a biomimetic chip that may be used for drug testing for treating various uterine diseases or for patient-specific treatment.

While the present disclosure has been described herein with a focus on limited embodiments, various embodiments are possible within the scope of the present disclosure. In addition, although not explicitly described in the present specification, equivalents to the embodiments are also incorporated into the present disclosure as they are. Therefore, the scope of the present disclosure are defined by the following claims.

INDUSTRIAL APPLICABILITY

The present disclosure may be used in industries related to microfluidic chips.

The invention claimed is:

1. A three-dimensional biomimetic chip for simulating an endometrium, the three-dimensional biomimetic chip comprising a plurality of chambers, and a plurality of posts, which are arranged between the plurality of chambers,
   wherein the plurality of chambers comprises a third cell culture chamber, a first culture medium chamber, a second cell culture chamber, a first cell culture chamber, and a second culture medium chamber,
   wherein the first cell culture chamber comprises a first culture channel in which uterine vascular endothelial cells are cultured;
   wherein the second cell culture chamber comprises a second culture channel that communicates with the first culture channel and in which endometrial stromal fibroblasts are cultured;
   wherein the first culture medium chamber comprises a first culture medium channel that communicates with the second culture channel, into which a culture medium is injected, and in which endometrial epithelial cells are cultured,
   wherein the third cell culture chamber comprises a third culture channel that communicates with the first culture medium channel, and in which endometrial stromal fibroblast are cultured, and
   wherein the second culture medium chamber comprises a second culture medium channel that communicates with the first culture channel, and into which a culture medium is injected,
   wherein the third culture channel and the second culture medium channel are each the outermost channels among the plurality of channels comprised in the plurality of chambers,
   wherein the second culture channel and the third culture channel are positioned on one side of the first culture channel in one direction, and growth of blood vessels formed by uterine vascular endothelial cells in the first culture channel is oriented in the one direction,
   wherein the plurality of the posts comprises:
   a plurality of first posts arranged along a boundary between the first culture channel and the second culture channel, a plurality of second posts arranged along a boundary between the second culture channel and the first culture medium channel, and a plurality of third posts arranged along a boundary between the first culture medium channel and the third culture channel, wherein each of the plurality of posts comprises a polygonal prism shape comprising one curved surface that curves toward the interior of adjacent channel, and wherein curved surfaces of the plurality of second posts and the plurality of third posts face in opposite directions, and embryos injected into the first culture medium channel roll on the curved surfaces of the plurality of second posts and the plurality of third posts.

2. The three-dimensional biomimetic chip of claim 1, wherein the first culture channel, the second culture channel, and the first culture medium channel are formed into one body.

3. The three-dimensional biomimetic chip of claim 1, wherein the plurality of first posts is arranged at a first gap, and
the plurality of second posts is arranged at a second gap, and wherein the second gap is greater than the first gap.

4. A method of three-dimensionally simulating an endometrium by culturing cells in a third cell culture chamber, a first culture medium chamber, a second cell culture chamber, a first cell culture chamber, and a second culture medium chamber, the method comprising:

culturing uterine vascular endothelial cells in the first cell culture chamber, wherein the first cell culture chamber comprises a first culture channel in which uterine vascular endothelial cells are cultured;

culturing endometrial stromal fibroblasts in the second cell culture chamber, wherein the second cell culture comprises a second culture channel that communicates with the first culture channel and in which endometrial stromal fibroblasts are cultured;

injecting a culture medium into the first and second culture medium chamber, wherein the first culture medium chamber comprises a first culture medium channel that communicates with the second culture channel, into which a culture medium is injected, and in which endometrial epithelial cells are cultured, wherein the second culture medium chamber comprises a second culture medium channel that communicates with the first culture channel, and into which a culture medium is injected;

culturing endometrial stromal fibroblasts in the third cell culture chamber, wherein the third cell culture chamber is on one side of the first culture medium chamber, and comprises a third culture channel that communicates with the first culture medium channel and in which endometrial stromal fibroblasts are cultured;

culturing endometrial epithelial cells in the first culture medium chamber;

growing blood vessels formed by uterine vascular endothelial cells in the first culture channel, wherein the second culture channel and the third culture channel are positioned on one side of the first culture channel in one direction and blood vessels are oriented in the one direction;

wherein the third culture channel and the second culture medium channel are each the outermost channels among the plurality of channels comprised in the plurality of chambers, wherein the plurality of the posts comprises:

a plurality of first posts arranged along a boundary between the first culture channel and the second culture channel, a plurality of second posts arranged along a boundary between the second culture channel and the first culture medium channel, and a plurality of third posts arranged along a boundary between the first culture medium channel and the third culture channel, wherein each of the plurality of posts comprises a polygonal prism shape comprising one curved surface that curves toward the interior of adjacent channel, and further comprising injecting embryos into the first culture medium channel, wherein curved surfaces of the plurality of second posts and the plurality of third posts face in opposite directions and embryos roll on the curved surface of the plurality of second posts and the plurality of third posts.

5. The method of claim 4, wherein after culturing uterine vascular endothelial cells and endometrial stromal fibroblasts, after a first period, culturing endometrial epithelial cells, wherein the first period is a period during which the second cells perform self-assembly in the second cell culture chamber, thereby forming blood vessels in the first cell culture chamber.

* * * * *